United States Patent
Stock et al.

(10) Patent No.: US 9,316,614 B2
(45) Date of Patent: Apr. 19, 2016

(54) ALCOHOL-MEASURING DEVICE WITH FAST OPERATIONAL READINESS

(71) Applicant: Dräger Safety AG & Co. KGaA, Lübeck (DE)

(72) Inventors: Burkhard Stock, Lübeck (DE); Jens Rekow, Lübeck (DE)

(73) Assignee: Dräger Safety AG & Co. KGaA, Lübeck (DE)

( * ) Notice: Subject to any disclaimer, the term of this patent is extended or adjusted under 35 U.S.C. 154(b) by 404 days.

(21) Appl. No.: 14/018,875

(22) Filed: Sep. 5, 2013

(65) Prior Publication Data
US 2014/0061043 A1    Mar. 6, 2014

(30) Foreign Application Priority Data
Sep. 6, 2012  (DE) .......................... 10 2012 017 638

(51) Int. Cl.
| | |
|---|---|
| *G01N 27/416* | (2006.01) |
| *G01N 33/497* | (2006.01) |
| *A61B 5/08* | (2006.01) |
| *A61B 5/091* | (2006.01) |
| *A61B 5/00* | (2006.01) |

(52) U.S. Cl.
CPC ............ *G01N 27/4162* (2013.01); *A61B 5/082* (2013.01); *G01N 33/497* (2013.01); *A61B 5/091* (2013.01); *A61B 5/4845* (2013.01)

(58) Field of Classification Search
CPC ........... G01N 27/416–27/4162; G01N 22/497; G01N 22/4972; A61B 5/082; A61B 5/091–5/097; A61B 5/4845
See application file for complete search history.

(56) References Cited

U.S. PATENT DOCUMENTS

| 4,770,026 A | 9/1988 | Wolf |
|---|---|---|
| 5,759,368 A | 6/1998 | Kühn |

FOREIGN PATENT DOCUMENTS

| DE | 196 19 169 C2 | 7/1998 |
|---|---|---|
| EP | 1 326 075 A1 | 7/2003 |
| WO | 92/22813 A1 | 12/1992 |

*Primary Examiner* — J. Christopher Ball
*Assistant Examiner* — Maris R Kessel
(74) *Attorney, Agent, or Firm* — McGlew and Tuttle, P.C.

(57) ABSTRACT

An alcohol-measuring device includes a mouthpiece (1), designed to enable a test subject to release breathing air into the mouthpiece, an electrochemical sensor (6), in fluidic connection with the mouthpiece (1) to measure alcohol in the breathing air of the test subject and a control unit. The sensor (6) has at least two heating elements (9, 10), one heating element arranged on the front side and one heating element arranged on the rear side of the sensor (6). The control unit (4) is electrically connected to the heating elements to supply electrical energy for the heating elements. The control unit (4) is set up to heat the heating elements each to a desired temperature. The control unit (4) is also electrically connected to the sensor (6) in order to determine the value of the alcohol concentration in the breathing air of the test subject.

19 Claims, 2 Drawing Sheets

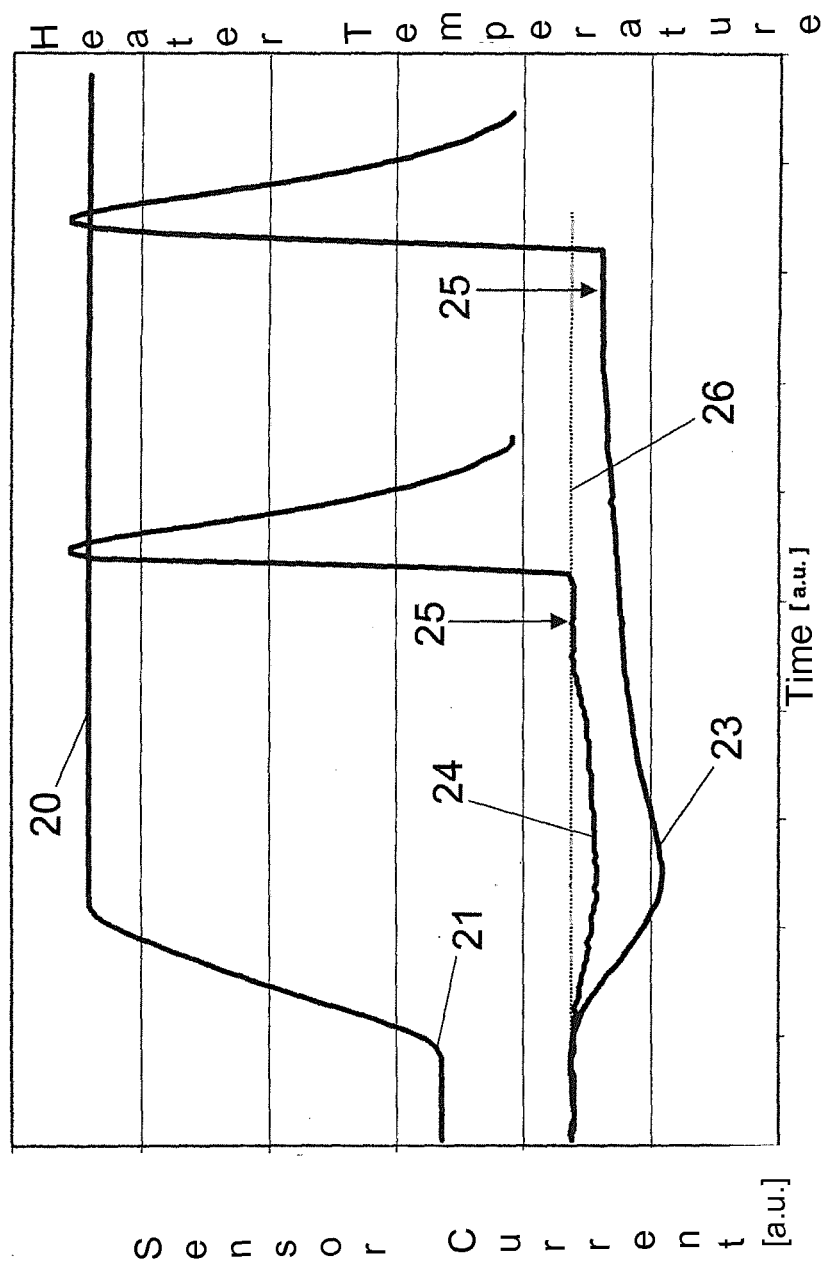

ALCOHOL-MEASURING DEVICE WITH FAST OPERATIONAL READINESS

CROSS REFERENCE TO RELATED APPLICATIONS

This application claims the benefit of priority under 35 U.S.C. §119 of German Patent Application DE 10 2012 017 638.4 filed Sep. 6, 2012, the entire contents of which are incorporated herein by reference.

FIELD OF THE INVENTION

The present invention pertains to an alcohol-measuring device, which is provided with an electrochemical sensor and is designed to achieve fast operational readiness of the measuring device.

BACKGROUND OF THE INVENTION

DE 196 19 169 C2 describes an electrochemical gas sensor with at least two electrodes, with an electrode support and with an electrolyte in a housing made of a material impermeable to the electrolyte: the otherwise closed housing has only one inlet and outlet capillary each for the gas to be measured. Furthermore, a heater and the working electrode are arranged in the housing in the flow path between the inlet capillary and the outlet capillary, wherein the heater forms a gap with the working electrode, and wherein the electrode array with the counterelectrode or additionally with the reference electrode is arranged on the side facing away from the gap in relation to the working electrode.

EP 1 326 075 A1 pertains to a device for measuring the alcohol vapor concentration in a sample, wherein the device has an electrochemical sensor for monitoring the alcohol by a diffusion current, means for determining the limiting diffusion current and means for generating an alcohol vapor concentration signal from the limiting diffusion current determined.

WO 92/22813 A1 describes a breath alcohol analyzing device with a sample chamber for collecting a breath sample, with a breath alcohol detector and with electronic means for processing data from the sample chamber and from the breath alcohol detector. The device has, besides, means for heating the sample chamber and/or the breath alcohol detector. The device can be used to influence the operation of a vehicle if the alcohol in the breath sample exceeds a preset limit.

In prior-art devices for measuring the breath alcohol concentration (alcohol-measuring device or breath alcohol-measuring device for short), the alcohol concentration in the air expired by a test subject is measured by means of indirect measurement methods, for example, by the electrochemical reaction of the alcohol molecules contained in the expired air in a measuring cell (electrochemical sensor). The method for breath alcohol determination by means of an electrochemical sensor is based on the principle of a fuel cell. For example, a piston (pump) driven by an electric motor delivers for this an air sample of the expired air with an exactly set volume (e.g., 1 $cm^3$) into a sampling chamber. The electrochemical sensor analyzes the breath sample with the highest possible accuracy for the quantity of ethanol contained in the breath sample. A measuring electrode, a counterelectrode, a membrane located between these electrodes and a small quantity of electrolyte are present in the sensor (i.e., the sensor housing). The electrolyte and the electrode material are selected to be such that the substance to be analyzed (alcohol or ethanol) is electrochemically oxidized on the catalyst layer of the measuring electrode. The electrons being released during the reaction now flow over the connection wires of the sensor (i.e., connection wires of the measuring electrode and of the counterelectrode) as an electrical current to an analyzing unit of the alcohol-measuring device, where the electrode current can be measured, for example, over a load resistance. The total electric charge reacted in the electrochemical reaction is determined during the analysis of the sensor current. The sensor current is integrated over time in the case of this so-called coulometry, and the time integral corresponds to the area under the sensor current curve.

For example, a pressure sensor is used to determine the breath volume of the test subject. A dynamic pressure, which increases with increasing respiratory flow, develops due to the respiratory flow in front of a narrowing (diaphragm) in the gas path in the measuring device (e.g., in the mouthpiece). This dynamic pressure is determined with the pressure sensor and is an indicator of the value of the respiratory flow.

At low temperatures (e.g., <0° C.), the above-described electrochemical sensor of an alcohol-measuring device must at first be heated in order to make possible a reliable measurement of the alcohol concentration in the air expired by the test subject, because the rate of the chemical reaction in the sensor decreases greatly with decreasing temperature and thus makes it difficult to accurately analyze the sensor signals. The temperature of the sensor should be at least 0° C. for a reliable measurement. The necessary heating of the electrochemical sensor was carried out hitherto by placing a single heating element on the rear side of the sensor.

However, it was found that even if the sensor has reached its necessary temperature of at least 0°, the sensor yields sufficiently accurate measurement results only a certain time period after that temperature had been reached in prior-art alcohol-measuring devices. Consequently, it is necessary to wait a relatively long time after switching on the measuring device (i.e., after switching on the heating element to heat the sensor) before the measuring device becomes ready to operate in order to make it possible to carry out a reliable measurement of the breath alcohol concentration. This is felt to be very disturbing especially in case of interlock systems in motor vehicles, in which the engine of the vehicle can be started only after a breath test for measuring the breath alcohol concentration. There was no explanation so far for this undesired, long delay until the operational readiness is reached.

SUMMARY OF THE INVENTION

A basic object of the present invention is therefore to make available an alcohol-measuring device with an electrochemical sensor, which is set up to achieve fast operational readiness of the alcohol-measuring device.

This is achieved according to the present invention by the electrochemical sensor of the measuring device being provided with at least one heating element each for heating up the electrochemical sensor on both its front side and its rear side. A higher flow of energy through the sensor and hence faster heating of the sensor are advantageously achieved due to the larger surface or contact surface of the heating elements provided on both sides. In addition, it is possible to minimize a temperature gradient developing due to the external heating of the sensor over the sensor or over a membrane within the sensor by means of a suitable actuation of the heating elements. The inventors have found that a high temperature gradient, which leads to an undesired, thermally induced sensor current (Ludwig-Soret effect), by which the sensor signal proper is noticeably distorted, will develop over the sensor membrane in case of a conventional, one-sided heating by means of only one heating element.

According to the invention, an alcohol-measuring device is provided comprising mouthpiece to receive breathing air, an electrochemical sensor in fluidic connection with the mouthpiece to measure alcohol in the breathing air of the test subject and a heating arrangement heating plural sides of the electrochemical sensor for reducing a temperature gradient, over the sensor or over a sensor membrane, in a direction between the sides of the electrochemical sensor. A control unit is electrically connected to the heating arrangement in order to supply electrical energy to the heating arrangement to control heat supplied to the sides of the electrochemical sensor. The control unit is electrically connected to the electrochemical sensor to determine a value of an alcohol concentration in the breathing air of the test subject.

An essential drawback of the prior-art solution is that in case of heating the electrochemical sensor on one side by means of only a single heating element on the outer side of the sensor or of the sensor housing, the sensor only yields accurate measurement results after a certain time, so that the measuring device is only ready to operate after a rather long time delay. The cause of this is, as the inventors have found, that a temperature gradient is generated over the sensor and hence over the membrane of the sensor. This means that the front side and the rear side of the membrane of the sensor do not have the same temperature, so that there is a temperature gradient between the front side and the rear side of the membrane. As the inventors have found, a drift of ions from the warmer side in the direction of the colder side of the membrane of the sensor, which drift is described by the Ludwig-Soret effect, develops as a result, which leads to the generation of an additional current (i.e., in addition to the measured current proper) between the measuring electrode on one side of the membrane and the reference electrode on the opposite side of the membrane. This current interferes with the measurement of the alcohol concentration, during which the current generated by the reaction of the alcohol molecules is analyzed. It is consequently necessary to wait until the temperature gradient disappears due to the heating of the sensor and thus the thermally induced sensor current over the membrane of the sensor also disappears before the alcohol-measuring device is ready to operate and an alcohol measurement can be started. The sensor must be heated through uniformly for this, so that the front side and the rear side of the sensor membrane have essentially the same temperature. The time needed for the temperature gradient to disappear is often longer than the actual time during which the sensor is heated up and thus it leads to an undesired delay in the measuring device becoming ready to operate. This problem is solved according to the present invention by at least one heating element on both the front side and the rear side of the sensor.

The sensor can be heated up very fast in his manner and the disadvantageous temperature gradient can at the same time be reduced very fast to a minimum, as a result of which very fast operational readiness of the measuring device is achieved.

According to the present invention, the alcohol-measuring device has a mouthpiece, which is designed for a test subject to be able to blow breathing air into the mouthpiece. This mouthpiece is in fluidic connection with an electrochemical sensor, which is designed to measure alcohol in the test subject's breathing air, and which has a front side and a rear side. At least one heating element is arranged on the front side of the sensor, and at least one heating element is arranged on the rear side of the sensor. It is also possible, however, that heating elements are additionally arranged on the lateral surfaces of the sensor. The position and number of heating elements depend essentially on the geometry of the sensor or sensor housing.

It is essential for the number of the heating elements and their positioning that heating of the sensor be achieved as fast as possible in order to reduce the temperature gradient over the sensor membrane to a minimum as fast as possible. Thus, it may be advantageous, for example, to arrange two heating elements on the rear side of the sensor housing and only one heating element on the front side if the membrane is located closer to the front side of the sensor in the interior of the sensor. As an alternative, the heating elements may also be of different size or have different heat outputs. For example, a heat-conducting paste or an adhesive with good heat-conducting properties may be used to achieve the best possible heat transfer between the heating elements and the sensor surface. What is essential for the above-described embodiments is to minimize the temperature gradient over the sensor membrane as fast as possible.

The measuring device has, besides, a control unit, which is electrically conducted with the heating elements in order to supply electric energy to the heating elements in order to thus heat the heating elements to a desired temperature. The temperature of the heating elements arranged on the front side and on the rear side of the sensor may be equal or different, which depends, among other things, on the construction of the sensor and/or on the position of the sensor membrane in the interior of the sensor. To determine the temperature or heat output of the respective heating elements, experiments were carried out with the aim of reducing the temperature gradients over the sensor membrane to a desired minimum as fast as possible. Different energy values were fed for this purpose to the heating elements in a number of measurement series. The optimal values found are subsequently stored in a memory of the control unit. In addition, the control unit is electrically connected to the sensor in order to determine the value of the alcohol concentration in the test subject's breathing air.

The mouthpiece is preferably in fluidic connection with a pressure sensor, which is electrically connected to the control unit in order to determine the breath volume of the breathing air blown by the test subject into the mouthpiece.

In a preferred embodiment, the measuring device according to the present invention has a pump, which is in fluidic connection with the sensor in order to deliver a desired quantity of breathing air into the sensor, with the pump being controlled by the control unit.

As was explained above, the control unit is preferably designed to heat the sensor by means of the heating elements to a suitable operating temperature as fast as possible and to reduce at the same time the temperature gradient over the sensor, and preferably over the membrane of the sensor, to a desired minimum as fast as possible. The determination of the alcohol concentration is performed only when the temperature gradient has a desired minimum (the alcohol-measuring device is ready to operate).

At least one of the heating elements is preferably coupled with a temperature sensor in order to detect the temperature of this at least one heating element, with each temperature sensor being electrically connected to the control unit. However, a temperature sensor each may also be provided at a plurality of heating elements or at each of the heating elements. The temperatures at the heating elements provided with a temperature sensor can be accurately detected and adjusted in this manner. If, for example, only one of the heating elements is provided with a temperature sensor, the temperature of this heating element can be adjusted to a desired temperature. The temperature of the heating element of the other heating element or heating elements can then be controlled such that the temperature gradient over the sensor or the membrane will reach a minimum as fast as possible.

In case of a symmetrical design of the sensor, the heating elements on the front side and on the rear side of the sensor is adjusted to the same temperature, because the temperature gradient over the sensor is essentially equal in this case to the temperature gradient over the membrane. If, however, the sensor has an asymmetric design, i.e., the membrane is not arranged in the middle between the front side and the rear side of the sensor, it may be advantageous to adjust the heating elements on the front side and the rear side of the sensor to different temperatures. Based on the asymmetric heat capacity on the two sides of the membrane, a very fast reduction of the temperature gradient over the membrane is achieved hereby, so that the measuring device will be ready to operate in a very short time. The different temperature values of the heating elements can be determined experimentally and stored in a memory of the control unit.

It is apparent that the temperature sensor or temperature sensors do not have to be arranged directly on the heating elements. The temperature sensor or temperature sensors may also be positioned at other points of the sensor or in the interior of the measuring device.

The present invention will now be described on the basis of an exemplary embodiment with reference to the figures, on the basis of which an exemplary embodiment of the alcohol-measuring device according to the present invention will be explained. However, the present invention is not limited to this exemplary embodiment. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

FIG. 2 is a diagram showing the sensor signals in case of one-sided and two-sided heating during the heating and after exposure to alcohol, as well as the curve of the temperature of one of the heating elements.

DESCRIPTION OF THE PREFERRED EMBODIMENTS

Figure 1:
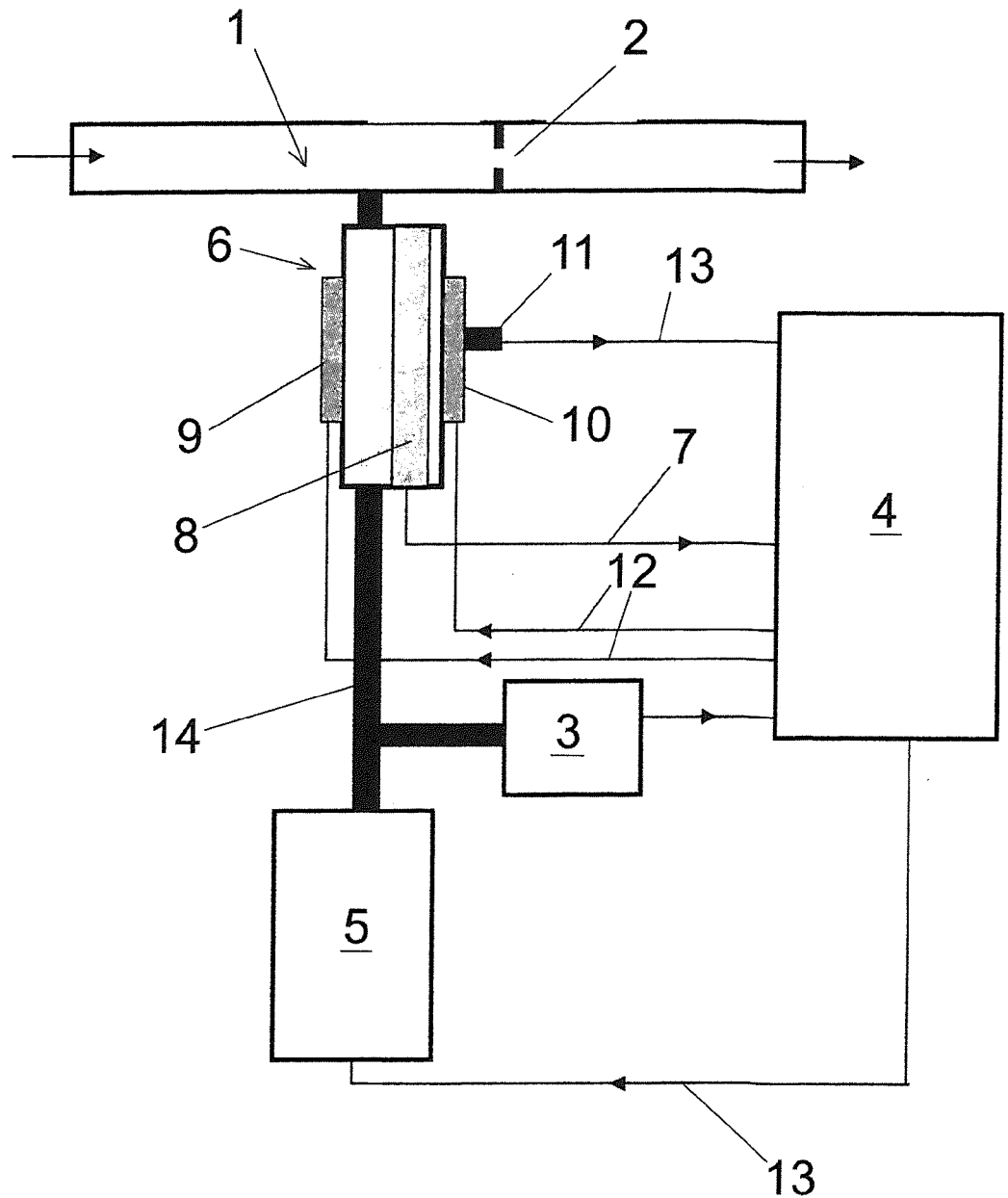
FIG. 1 is a view of the design of an alcohol-measuring device according to the invention, with a sensor heated on both sides.

Referring to the drawings in particular, the alcohol-measuring device according to the present invention, whose design is shown in FIG. 1, has a replaceable mouthpiece 1, which is connected via a fluidic connection 14 with an electrochemical sensor 6, with a pressure sensor 3 and with a pump 5. To measure the breath alcohol concentration, the test subject to be tested blows his breathing air into the left end of the mouthpiece, as is indicated by arrows in FIG. 1. The dynamic pressure produced by the breath flow at the diaphragm 2 within the mouthpiece 1 is measured with the pressure sensor 3 and converted into a breath flow value in an analyzing unit, which is electrically connected to the pressure sensor 3 and which may be part of a control unit 4. If the test subject has released a sufficient quantity of breathing air, a defined sample (e.g., 1 cm$^3$) is drawn from the breathing air into the electrochemical sensor 6 with pump 5. The pump 5 is controlled for this by the control unit 4 via the control line 13. As was described in the introduction, the alcohol molecules are absorbed on the surface of the sensor 6 and subsequently reacted electrochemically. The electric current of the sensor 6, which is generated hereby at the terminals of the measuring electrode and of the counterelectrode, is sent via a measuring line 7 to the analyzing unit and analyzed according to prior-art methods, as is described, for example, in U.S. Pat. No. 4,770,026 (U.S. Pat. No. 4,770,026 is hereby incorporated by reference in its entirety). A heating element 9, 10 is arranged permanently on the front side and on the rear side of sensor 6, and the two heating elements 9, 10 are actuated by the control unit 4 via corresponding control lines 12. In addition, a temperature sensor 11, which is likewise connected to the control unit 4, is located on one of the heating elements 10 in order to make it possible to measure the temperature of the heating element 10. It is also possible that a temperature sensor each is arranged at both heating elements 9, 10 in order to make it possible to measure the temperature of both heating elements. The heating elements and the temperature sensors are preferably fastened with a heat-conducting paste or with a heat-conducting adhesive.

As was explained above, sensor 6 must be heated at low temperatures (for example, <0° C.) by supplying electric energy. The quantity of energy that flows into sensor 6 can be controlled, for example, via the temperature of the heating elements 9, 10 and via the length duration of the heating time. However, the quantity of energy can also be controlled via corresponding values of the voltage/current and the heating time, which are stored in the control unit 4, for example, in a table, if, for example, no temperature sensors are provided. Since the quantity of energy to be supplied also depends on the temperature of the environment in which the measuring device is operated, it is advantageous to provide a temperature sensor that measures this ambient temperature. This sensor may be arranged somewhere in or at the housing of the measuring device. If the alcohol-measuring device is provided, for example, as part of an interlock system in a motor vehicle, the measuring device may be provided or connected with a temperature sensor in order to measure the temperature in the interior of the vehicle. A larger quantity of energy must be supplied to the heating elements at low temperature than at high temperatures. The heating elements 9, 10 of the sensor may be designed, for example, as electric resistance heating elements.

The energy E_therm, which is fed to the sensor 6 via the heating elements 9, 10, is the product of the heat transfer coefficient a of the membrane of sensor 6, the area A of the heating elements 9, 10 as well as the time integral over the temperature difference dT(t) between the heating elements and the membrane 8 of the sensor. The upper integration limit t denotes the time interval being considered:

$$\text{E\_therm} = aA \int_0^t dT(t)dt. \quad \text{(Equation 1)}$$

The temperature sensor 11 makes it possible to detect the temperature of the heating element 10 and to adjust the heating elements 9, 10 to a fixed temperature, and said heating elements 9, 10 may be adjusted to the same temperature or to different temperatures. Adjustment to a fixed temperature is necessary to reach a thermal equilibrium in the sensor membrane. The temperature gradient and hence also the thermally induced current can be minimized in this manner. As was described, heating element 9 may also be provided with a temperature sensor. As a result, the rapid minimization of the temperature gradient can be improved, especially if the constant temperatures of the two heating elements shall be different.

In addition, the measurement of the initial temperature of the sensor membrane 8 by means of the temperature sensor 11 is important. This value of the initial temperature is necessary for determining the minimum quantity of energy necessary for heating the sensor, because the energy necessary for heating membrane 8 to the minimum temperature of about 0° C. depends on the initial temperature of said membrane.

The control unit 4 therefore determines the initial temperature of the sensor by means of the temperature sensor 11 before the heating elements are switched on. As long as the heating elements 9, 10 are not yet switched on, sensor 6 and heating elements 9, 10 are in thermal equilibrium with one another due to their being in contact (i.e., they have the same temperature). The desired temperature T_soll of sensor 6 (e.g., 30° C.) and the energy value E_min are selected corresponding to a table being stored in the control unit 4. The values in the table are determined experimentally during the development of the alcohol-measuring device such that the shortest possible heat-up time is obtained for reaching the minimum temperature of about 0° C. These values in the table depend on the construction of the sensor and on other parameters.

Example

| T_start | T_soll | E_min | Heat-up time |
| --- | --- | --- | --- |
| −5° C. | 20° C. | 30 Wsec | 20 sec |
| −40° C. | 45° C. | 150 Wsec | 90 sec |

The temperature of the heating elements 9, 10 and the quantity of energy flowing into the membrane 8 are determined according to Equation 1 during the heating up. After the desired temperature T_soll and the minimum energy value E_min have been reached, the alcohol-measuring device tests the sensor signal and signals the operational readiness in case of sufficient stability.

With the introduction of E_min, the evaluation of the heat-up operation becomes independent from the time elapsing until T_soll is reached, because only the energy transferred into sensor 6 is detected independently from the time. This is especially important in interlock systems in which the supply voltage for the heating elements 9, 10 fluctuates greatly depending on the temperature and the state of the vehicle battery. Since the power dissipated in the heating elements is a quadratic function of the voltage, greatly different times elapsing until T_soll is reached are also obtained. A fixed heating time would not be advantageous here.

The two-sided heating of sensor 6 by means of the heating elements 9, 10 arranged on both sides has the advantage in this case that twice as much thermal power flows into the sensor due to the larger (i.e., twice as large) contact area, i.e., the sensor is heated markedly faster. Even this could also be achieved by means of a higher output and/or a larger contact area of the heating element arranged on one side, this could be achieved only with the drawback of a much greater temperature gradient over the sensor (and hence over the membrane) and a great drift of the sensor signal, which is associated herewith, due to the thermally induced current. Thus, a faster heat-up time or a shorter time needed to reach the operating state cannot consequently be achieved. Even if the heating elements are arranged on both sides, rapid minimization of the temperature gradient to reach a fast operational readiness of the measuring device can only be guaranteed if the heating elements are adjusted such that the temperature gradient reaches the desired minimum as fast as possible. This is especially important if the sensor possesses thermally symmetrical properties.

After the alcohol-measuring device according to the present invention has been switched on, the control unit 4 at first checks by means of the temperature sensor 11 whether the temperature of sensor 6 is so low (i.e., <0° C.) that sensor 6 must be heated. The control unit 4 switches on the heating elements 9, 10 in this case. In the sensor has reached the desired temperature, the heat output of the heating elements is reduced in order to maintain the temperature of the heating elements at the desired value, and the operational readiness of the measuring device is signaled when the temperature gradient has reached the desired minimum that is necessary for performing an accurate measurement of the breath alcohol concentration. This signaling may take place visually or acoustically.

The difference between one-sided and two-sided heating is shown in FIG. 2. The sensor current is plotted in the view according to FIG. 2 on the y axis on the left side and the temperature of the heating elements on the y axis on the right side, while the time curve is shown on the x axis. The temperature of the heating elements is represented by curve 20 in FIG. 2. When the heating elements 9, 10 (point 21) are switched on, the temperature of the heating elements 9, 10 rises greatly. When the desired temperature (e.g., 30° C.) is reached at point 22, the control unit 4 adjusts the heating element 10 to a constant temperature (represented by the horizontal temperature curve indicated by line 20). Heating element 9 is actuated simultaneously with heating element 10 and thus likewise adjusted to a constant temperature. The constant temperature of heating element 9 is preferably equal to the constant temperature of heating element 10, but it may also deviate from the constant temperature of heating element 9, doing so depending on the design and the thermal properties of sensor 6.

The curve of the sensor current of a sensor heated on one side is designated by reference number 23, whereas curve 24 represents the sensor current of a sensor heated on both sides. Shortly after the heating element or heating elements has/have been switched on, there is a slight change in the sensor signal, which is represented by the reduction of the sensor current in FIG. 2. As was mentioned already, this effect is, however, markedly more pronounced in case of one-sided heating (curve 23) than in case of two-sided heating (curve 24), because the temperature gradient over the membrane is markedly lower in case of two-sided heating, as was explained in detail above.

However, the alcohol-measuring device is ready for the alcohol measurement only when the sensor signal ceases to change too greatly. The additional, thermally induced current would otherwise lead to a distortion of the measurement, especially at low alcohol concentrations, at which the current signal is also very weak.

Control unit 4 therefore checks the change in the sensor signal over time during the heat-up operation. If the checking shows sufficient stability of the sensor signal, the readiness of the alcohol-measuring device for measurement is displayed. As is apparent from FIG. 2, this point indicating sufficient stability of the sensor signal is reached markedly sooner in case of two-sided heating, which is indicated by the arrows 25 in FIG. 2.

It can also be recognized from the auxiliary line 26 drawn as a broken line that even though the sensor signal is stable in case of one-sided heating when the operational readiness is reached, it does not return to the initial value, because, even though the temperature gradient becomes smaller with the progression of time in case of one-sided heating, it does not disappear altogether, and a thermally induced constant current therefore continues to be present. As expected, there continues to be a temperature gradient over the membrane. This does not happen in case of two-sided heating, and the sensor signal returns to the initial value when the operational readiness is reached. Consequently, a very much higher accuracy of measurement is reached in case of two-sided heating of the sensor.

If the test subject has released a sufficient quantity of breathing air into the alcohol-measuring device through the replaceable mouthpiece 1, pump 5 (also called sampling unit) draws a small quantity of gas (for example, 0.2-1 mL) into sensor 6. The dynamic pressure generated by the breath flow at the diaphragm 2 of the mouthpiece is detected by the pressure sensor 3 and converted into a breath volume in the control unit 4.

The signal (i.e., sensor current) rises rapidly to a maximum after the sensor 6 is exposed to the gas (readiness for measurement until the signal rises, e.g., 2 sec) and subsequently drops exponentially, as this is described, for example, in U.S. Pat. No. 4,770,026. When the signal has dropped to about 20% of the maximum, the measurement is terminated. The concentration of the alcohol in the breath sample is calculated in the known manner from the area under the curve.

As was explained above, the membrane must be heated uniformly on the front side and on the rear side in order to obtain the smallest possible temperature gradient over the membrane 8 of the sensor. However, since the electrochemical sensor 6 does not usually have a symmetrical design in respect to the heat transmission resistance (i.e., heating element-housing-membrane), the temperature of the heating elements 9, 10 must be different on the front side and on the rear side of sensor 6 for a negligible sensor current, i.e., equal thermal flux on both sides of the membrane. The difference in the temperatures of the two heating elements 9, 10 can be determined, for example, experimentally.

The different temperatures of the two heating elements 9, 10 can be achieved by the two heating elements 9, 10 being actuated differently by the control unit 4 (e.g., pulse width modulation), so that the power dissipated in the heating elements is not equal.

Another (albeit more complicated) method is to provide both heating elements 9, 10 with a temperature sensor 11 each and to obtain the different energy flux by different desired temperatures of the two heating elements.

The different desired temperatures or powers must be determined experimentally in both cases and stored permanently in the alcohol-measuring device.

An active adjustment during heating would also be possible, in which case the power of the heating elements is adjusted such that the thermally induced current becomes as weak as possible. However, this solution is very difficult especially in case of short heat-up times because of the thermal inertia.

Finally, it should be noted that three or more heating elements may also be provided at the electrochemical sensor instead of the two heating elements described, which are arranged on the front side and on the rear side of the sensor. This may be necessary in some cases and in certain sensor configurations in order to achieve a better heat distribution and consequently a lower temperature gradient.

While specific embodiments of the invention have been shown and described in detail to illustrate the application of the principles of the invention, it will be understood that the invention may be embodied otherwise without departing from such principles.

APPENDIX

List of Reference Numbers

| | |
|---|---|
| 1 | Mouthpiece |
| 2 | Diaphragm |
| 3 | Pressure sensor |
| 4 | Control unit |
| 5 | Pump |
| 6 | Sensor |
| 7 | Measuring line |
| 8 | Membrane |
| 9 | Heating element |
| 10 | Heating element |
| 11 | Temperature sensor |
| 12 | Control lines |
| 13 | Control line |
| 14 | Fluidic connection |
| 20 | Temperature curve |
| 21 | Switching on of the heating elements |
| 22 | Reaching of the desired temperature |
| 23 | Sensor signal in case of one-sided heating |
| 24 | Sensor signal in case of two-sided heating |
| 25 | Stabilization of the sensor current |
| 26 | Auxiliary line |

What is claimed is:

1. An alcohol-measuring device comprising:
a mouthpiece designed to enable a test subject to release breathing air into the mouthpiece;
an electrochemical sensor in fluidic connection with the mouthpiece and designed to measure alcohol in the breathing air of the test subject, wherein the electrochemical sensor has a front side and a rear side;
at least two heating elements, wherein at least one heating element is arranged on the front side of the sensor and at least one heating element is arranged on the rear side of the sensor; and
a control unit electrically connected to the at least two heating elements in order to supply electrical energy for the heating elements, wherein:
the control unit is set up to heat the at least two heating elements each to a desired temperature; and
the control unit is electrically connected to the electrochemical sensor in order to determine the value of the alcohol concentration in the breathing air of the test subject.

2. An alcohol-measuring device in accordance with claim 1, further comprising a pressure sensor wherein the mouthpiece is in fluidic connection with the pressure sensor and the pressure sensor is electrically connected to the control unit in order to determine the volume of the breathing air released by the test subject into the mouthpiece.

3. An alcohol-measuring device in accordance with claim 1, wherein the control unit is set up to heat the sensor by means of the heating elements such that a temperature gradient over the sensor or over a sensor membrane reaches a desired minimum as fast as possible.

4. An alcohol-measuring device in accordance with claim 1, wherein the determination of the alcohol concentration is performed only when a temperature gradient over the sensor or over a sensor membrane has reached a desired minimum.

5. An alcohol-measuring device in accordance with claim 1, further comprising a pump in fluidic connection with the sensor in order to send a desired quantity of breathing air into the sensor, and which is controlled by the control unit.

6. An alcohol-measuring device in accordance with claim 1, further comprising at least one temperature sensor coupled with at least one of the at least two heating elements in order to detect the temperature of the at least one heating element, wherein the at least one temperature sensor is electrically connected to the control unit.

7. An alcohol-measuring device in accordance with claim 1, further comprising a temperature sensor arranged at each of the heating elements in order to detect the temperature of the respective heating elements, wherein each of the temperature sensors is electrically connected to the control unit.

8. An alcohol-measuring device in accordance with claim 1, wherein the heating elements comprise electrical resistance heating elements.

9. An alcohol-measuring device in accordance with claim 1, wherein a quantity of energy E_therm, which is calculated by means of the formula:

$$\text{E\_therm} = aA \int_0^t dT(t)dt$$

wherein a is the heat transfer coefficient of a membrane of the sensor, A is the area of the heating elements, t is the integration limit of the time interval, and dT(t) is the temperature difference between the heating elements and the membrane of the sensor, is fed to the heating elements.

10. An alcohol-measuring device in accordance with claim 1, wherein each of the heating elements is heated to an equal constant temperature in order to minimize the temperature gradient over the sensor or over a sensor membrane.

11. An alcohol-measuring device in accordance with claim 1, wherein the heating elements are heated to different constant temperatures in order to minimize the temperature gradient over the sensor or over a sensor membrane.

12. An alcohol-measuring device comprising:
a mouthpiece to receive breathing air from a test subject;
an electrochemical sensor in fluidic connection with the mouthpiece to measure alcohol in the breathing air of the test subject;
a heating arrangement comprising a plurality of electrical resistance heating elements heating plural sides of the electrochemical sensor for reducing a temperature gradient, over the sensor or over a sensor membrane, in a direction between the sides of the electrochemical sensor; and
a control unit electrically connected to the heating arrangement in order to supply electrical energy to the heating arrangement to control heat supplied to the sides of the electrochemical sensor, the control unit being electrically connected to the electrochemical sensor to determine a value of an alcohol concentration in the breathing air of the test subject.

13. An alcohol-measuring device in accordance with claim 12, further comprising a pressure sensor wherein the mouthpiece is in fluidic connection with the pressure sensor and the pressure sensor is electrically connected to the control unit to determine the volume of the breathing air released by the test subject into the mouthpiece.

14. An alcohol-measuring device in accordance with claim 12, wherein the determination of the alcohol concentration is performed only when a temperature gradient over the sensor or over a sensor membrane has reached a desired minimum.

15. An alcohol-measuring device in accordance with claim 12, further comprising a pump in fluidic connection with the sensor in order to send a desired quantity of breathing air to the sensor, and which is controlled by the control unit.

16. An alcohol-measuring device in accordance with claim 12, further comprising a temperature sensor coupled with the heating arrangement to detect a temperature of heating arrangement, wherein the temperature sensor is electrically connected to the control unit.

17. An alcohol-measuring device in accordance with claim 12, further comprising a temperature sensor arranged at or adjacent to the sides of the electrochemical sensor that are heated by the heating arrangement.

18. An alcohol-measuring device in accordance with claim 12, wherein a quantity of energy E_therm, which is calculated by means of the formula:

$$\text{E\_therm} = aA \int_0^t dT(t)dt$$

wherein a is the heat transfer coefficient of a membrane of the sensor, A is the area of the heating arrangement, t is the integration limit of the time interval, and dT(t) is the temperature difference between the heating arrangement and the membrane of the sensor, is fed to the heating arrangement.

19. An alcohol-measuring device in accordance with claim 12, wherein the heating arrangement is controlled whereby sides of the electrochemical sensor that are heated by the heating arrangement are heated to minimize the temperature gradient over the sensor or over a sensor membrane.

* * * * *